(12) United States Patent
Zhang et al.

(10) Patent No.: US 6,264,981 B1
(45) Date of Patent: Jul. 24, 2001

(54) ORAL TRANSMUCOSAL DRUG DOSAGE USING SOLID SOLUTION

(75) Inventors: Hao Zhang; Jed Croft, both of Salt Lake City, UT (US)

(73) Assignee: Anesta Corporation, Salt Lake City, UT (US)

( * ) Notice: Subject to any disclaimer, the term of this patent is extended or adjusted under 35 U.S.C. 154(b) by 0 days.

(21) Appl. No.: 09/428,071

(22) Filed: Oct. 27, 1999

(51) Int. Cl.⁷ ............................. A61K 9/48; A61K 9/20
(52) U.S. Cl. ............................. 424/451; 424/464
(58) Field of Search .................... 424/451, 464

(56) References Cited

U.S. PATENT DOCUMENTS

| | | | |
|---|---|---|---|
| 5,132,114 | 7/1992 | Stanley et al. | 424/440 |
| 5,354,560 | 10/1994 | Lovrecich | 424/489 |
| 5,449,521 | 9/1995 | Lovrecich | 424/489 |
| 5,711,961 | 1/1998 | Reiner et al. | 424/441 |

OTHER PUBLICATIONS

Krauskopf, K., "Introduction to Geochemistry" 2$^{nd}$ Ed., published by McGraw Hill, NY, pp. 114–117, (1979).
Stumm et al., "Aquotic Chemistry" published by Wiley Inter-Sci., NY, pp. 204–217 (1970).
Mason, Brian, "Principles of Geochemistry" 3$^{rd}$ Ed., published by John Wiley & Sons, NY, pp. 86–91 (1966).

*Primary Examiner*—Carlos Azpuru
(74) *Attorney, Agent, or Firm*—Kirton & McConkie; Michael F. Krieger

(57) ABSTRACT

The present invention is directed toward formulation and method for oral transmucosal delivery of a pharmaceutical. The invention provides a drug formulation comprising a solid pharmaceutical agent in solid solution with a dissolution agent. The formulation is administered into a patient's oral cavity, delivering the pharmaceutical agent by absorption through a patient's oral mucosal tissue. The formulation and method provide for improved oral mucosal delivery of the pharmaceutical agent.

55 Claims, 3 Drawing Sheets

ORAL TRANSMUCOSAL DRUG DOSAGE USING SOLID SOLUTION

BACKGROUND

1. Field of the Invention

The present invention relates to the improvement of oral transmucosal drug delivery systems. In particular, the invention relates to solid pharmaceutical dosage forms for oral transmucosal delivery of pharmaceutically active substances, and more particularly, to solid dosage forms producing higher dissolution rates and accordingly, higher absorption rates of the pharmaceutically active substance. Furthermore, the present invention provides improved solubility in saliva and mucosal absorption without compromising stability of the solid dosage form during storage.

2. Description of the Prior Art

Solid pharmaceutical dosage forms are well known in the art. Compared to other dosage forms, such as solutions (oral or injection) and vapor or gas inhalation, the oral solid dosage forms are the most preferred dosage forms and they account for eighty percent of all the pharmaceutical products on the market. Solid dosage forms are easier for patient or caregiver to identify, handle and administer. They are also non-invasive and have high patient compliance.

With respect to drug delivery routes, solid dosage forms can be further divided into several groups, gastrointestinal (GI) tract delivery, suppository (rectal, vaginal and urethral) delivery and oral transmucosal delivery. The majority of solid dosage forms on the market are designed for gastrointestinal delivery. GI delivery is often referred to simply as "oral delivery." Solids are also commonly delivered as suppositories such as laxatives, contraceptives and hemorrhoid medication. Relatively few drug formulations are designed as solid dosage forms intended to deliver a drug through the oral mucosa. Two such drug formulations are Oralet (®) and Actiq(®).

Despite the overall popularity of other delivery methods, oral transmucosal (OT) delivery is a particularly advantageous delivery route. One of the advantages of OT delivery is that it is a non-invasive drug delivery method. Furthermore, OT delivery has better patient compliance, less risk of infection and lower cost than invasive procedures such as injection and implantation. It also has much shorter onset time, i.e., the time from administration to therapeutic effect, than does oral delivery. A drug absorbed via the oral mucosa will also avoid first pass metabolism, in which the drug is metabolized in the GI tract and liver. Oral transmucosal delivery is simple and can be administered by the caregiver or the patient with minimal discomfort.

Various solid dosage forms, such as sublingual tablets, troches, lozenges, lozenges-on-a-stick, chewing gums, and buccal patches, have been used to deliver drugs via the oral mucosal tissue. U.S. Pat. No. 5,711,961 to Reiner, et al. discloses a chewing gum for the delivery of pharmaceuticals. The chewing gum delivery dosage form of Reiner is primarily directed for patients who may be more disposed to self-administer a drug in chewing gum form as opposed to other less familiar dosage forms. The gum may also be used to mask the taste of various pharmaceutical ingredients. Reiner also discloses the use of the gum formulation to extend the duration of drug delivery.

Transmucosal delivery of drugs is also accomplished through the use of patches which are attached using an adhesive to mucosal surfaces in the oral cavity. Oral transmucosal delivery using a buccal patch is disclosed in U.S. Pat. No. 5,298,256 to Flockhart, et al. The buccal patch may be designed as a "closed" delivery system, that is, the environmental conditions inside the patch are primarily controlled by the formulation. Employing a closed delivery system can facilitate drug delivery, such as allowing the use of enhancers or other permeability facilitators in the formulation which might otherwise be impractical. In an "open" delivery system, such as lozenges or sublingual tablets, the drug delivery conditions are influenced by the conditions of the surrounding environment, such as rate of saliva secretion, pH of the saliva, or other conditions beyond the control of the formulation. Buccal patch delivery also displays a pharmacokinetic delivery profile that can mimic a short term IV infusion.

Solid dosage forms such as lozenges and tablets are commonly used for oral transmucosal delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug.

A lozenge-on-a-stick dosage form of transmucosal drug delivery is disclosed in U.S. Pat. No. 4,671,953 to Stanley, et al. In addition to being non-invasive and providing a particularly easy method of delivery, the lozenge-on-a-stick dosage form allows a patient or caregiver to move the dose in and out of the mouth to titrate the dose. This practice is called dose-to-effect, in which a patient or caregiver controls the administration of the dose until the expected therapeutic effect is achieved. This is particularly important for certain symptoms, such as pain, nausea, motion sickness, and premedication prior to anesthesia because each patient needs a different amount of medication to treat these symptoms. For these types of treatments, the patient is the only one who knows how much medication is enough. Once the appropriate amount of drug is delivered, the patient or caregiver can remove the lozenge, thus, stopping the drug delivery to prevent overdose.

Solid dosage units are made in a number of ways. In a high volume manufacturing facility, solid dosage units can be made by direct compression, injection molding, freeze-drying or other solid processing techniques. Compression, by far, is the most commonly used manufacturing process in making solid dosage units. A typical formulation of solid dosage form consists of active ingredient(s), bulking agent (s), binder(s), flavor(s), lubricant(s) and other excipients.

To benefit from the advantages of oral transmucosal delivery, solid dosage forms must be formulated to take into account the oral cavity's unique environment. In certain aspects, the unique environment of the oral cavity can complicate the transmucosal delivery of the drug. For example, one of the significant aspects of the oral cavity environment with regard to its use as a drug administration route is that there is relatively little solvent into which a solid dosage form can dissolve. Furthermore, the relative amounts of saliva produced in given circumstances can vary widely. On the average, salivary glands produce between 800 to 1500 ml saliva a day. In a resting, unstimulated state, salivary glands produce about 0.5 ml mucous-type saliva per minute, while stimulated salivary glands produce about 1 to 3 ml per minute. During the time required for solid dose drug delivery, about 10 to 15 minutes, the total amount of saliva produced is 10 to 15 ml, which is a small volume compared to 600 to 1000 ml of potential solvent produced in the GI tract.

Similarly, there is a limited period of time during which the solid dosage form can be dissolved and absorbed. An orally (GI tract) delivered solid dose will remain in the GI tract 8 for several hours. An oral transmucosal dose remains in the oral cavity for a mere 10 to 15 minutes. During this period, the solid unit has to be dissolved, and the drug must be released and absorbed. This is a major challenge for formulating the transmucosal solid dosage form.

The absorption of a drug across the mucosal tissue can be described using the equation of Fick's first law:

$$\frac{dA}{dt} = \frac{DK_p}{h} \cdot (C_1 - C_2) \cdot S$$

where dA is the amount of drug delivered over time dt, $K_p$ is the partition coefficient of the drug between oral mucosal tissue and the drug solution, D is the diffusion coefficient of the drug inside the oral mucosal tissue, S is the surface area of the oral cavity, h is the thickness of the oral mucosal tissue, $C_1$ and $C_2$ are the drug concentrations in the solution and blood circulation, respectively.

The capacity of the oral transmucosal delivery is limited in large part by the surface area available for drug absorption. The surface area in the oral cavity is 200 $cm^2$, which is relatively small compared to the surface area of other drug delivery routes, such as the GI tract (350,000 $cm^2$) and skin (20,000 $cm^2$).

The contact time between the drug and the absorption surface is primarily controlled by the dissolution rate of the solid unit. Once the solid unit is dissolved, any drug solution not yet absorbed will be swallowed, thereby ending further OT drug absorption. Generally the time a solid unit can remain in the oral cavity is between 10 to 15 minutes, but this time period is quite variable and depends upon a number of factors. Some of the factors affecting the contact time are difficult to account for, such as how vigorously a patient will suck on the dosage form.

In addition to the difficulties presented by the oral cavity's unique environment, the physicochemical properties of the drug can present challenges and complications that affect oral transmucosal drug delivery. Primarily, the solubility, the dissolution rate, and the partition coefficient determine the extent to which a drug can be delivered via the oral mucosal tissue. Solubility and dissolution rate are key aspects in creating the concentration gradient, which is the driving force for drug delivery. Partition coefficient, on the other hand, acts like an amplifier, such that the drug delivery rate is directly proportional to the partition coefficient up to a point.

The solubility of a drug is an inherent characteristic of the drug in a particular solvent. The relative affinities of the solute molecules and the solid phases determine the solubility. In other words, the inter-molecular attractions between the solvent-solute and solute-solute molecules will largely determine solubility. The solubility of a drug is a specific thermodynamic property, that is, it describes the chemical state of the drug. Imbalance in a thermodynamic state will cause the change toward re-establishing a balance within the system. Because solubility is a specific thermodynamic quantity, any imbalance that causes a change away from solubility equilibrium will result in a change in the system toward re-establishing balance.

The partition coefficient is the concentration ratio of a drug between two phases. Partition coefficient is determined largely by the inherent properties of the drug. In the case of oral transmucosal delivery, the attraction of drug molecules between two phases on the solution/tissue interface determines the partition coefficient of the drug. As with solubility, partition coefficient is a thermodynamic property and any imbalance will cause a change toward re-establishing a balanced state.

The effectiveness of drug formulations is dependent upon the time frame imposed on the drug reaction. The dissolution rate of the drug, unlike the solubility and partition coefficient, is a kinetic property of a drug. An otherwise effective drug may have a dissolution rate which is acceptable for one delivery method but which is too slow for the particular time frame of another. For example the dissolution rate of a drug may be acceptable for GI delivery, but the dissolution rate may not be practical for oral transmucosal delivery. The time frame in oral transmucosal delivery is 10 to 15 minutes rather than 4 to 6 hours in the GI tract.

To a certain extent, the physicochemical properties of a drug can be manipulated by changing the surrounding environment. For example, the solubility of an ionizable drug can be greatly increased by changing the pH of the solution to a value at which the drug is in its ionized form. However, attempts to advantageously manipulate one particular physicochemical property can have a negative impact on another property. For instance, in designing a solid drug formulation, a pharmacist may attempt to increase the drug absorption by manipulating pH, but the altered pH negatively impacts other aspects of the formulation, such as the partition coefficient of the drug. Designing a solid, oral transmucosal formulation can be further complicated when a potentially effective solid formulation is unstable in storage and thereby rendered impractical for commercial use.

There are several ways drug designers attempt to increase solubility and dissolution rate. A common practice in the pharmaceutical industry is to use a co-solvent. Many drugs that are insoluble in aqueous media are more soluble in organic solvents. Formulations designed for intravenous injections often employ co-solvents to increase the solubility of drugs. However, solid dosage forms, by their nature, cannot be formed with co-solvents solubility.

Some relatively insoluble drugs can be combined with other molecules to form more soluble complexes. Cyclodextrins, for example, have been used in many formulations to increase the solubility of poorly soluble, hydrophobic drugs. Derivatized cyclodextrins are donut shaped molecules with a hydrophobic interior and hydrophilic exterior. Hydrophobic drugs can be sheltered inside the cyclodextrin cavity, and thus become soluble in the aqueous media.

One significant drawback to complexing is that once a drug molecule is complexed with another molecule, such as a hydrophobic drug inside a cyclodextrin, the drug is no longer a free molecule. In other words, complexing the drug allows the drug to go into solution, however, the complex often has poor absorption characteristics. This is often the case with cyclodextrin-complexed drugs. The drug alone may be capable of being absorbed, but due to its larger size, the drug/cyclodextrin complex is too large to be absorbed through the mucosa.

For weak acids or weak bases, which are ionizable, there is yet another way to manipulate the solubility and dissolution rate. The weak acid or weak base can react with base or acid, respectively, to form a salt. The ionized salt forms will almost always have higher solubilities and dissolution rates than the unionized forms. In many cases, they are also more stable chemically or physically. However, the ionized forms almost always have lower partition coefficients than the unionized forms, and therefore are less well absorbed by the oral mucosal tissue. Thus, converting the weak acid or base to an ionized form in order to increase solubility compromises absorption.

A common method of controlling the pH of the formulation is to use a buffer system. A buffer system consists of hydrogen ion donor(s) (acid) and conjugate hydrogen ion receiver(s) (base). An appropriate buffer system stabilizes the pH. However, optimizing the pH generally compromises the solubility and partition coefficient for oral transmucosal drug delivery.

It would be advantageous to design a solid oral transmucosal dosage that would allow for increased dissolution, solubility and stability of the drug and yet preserve the drug absorption rate. It would also be advantageous to provide a formulation concept and manufacturing processes for making solid dosage units embodying the foregoing attributes.

BRIEF SUMMARY AND OBJECTS OF THE INVENTION

In view of the foregoing, it is an object of at least one embodiment of the present invention to provide a method and formulation for oral transmucosal drug delivery of a solid that takes into account the unique environment of the oral cavity.

It is another object of at least one embodiment of the present invention to provide a method and formulation for oral transmucosal delivery of a solid that allows for improved dissolution.

It is another object of at least one embodiment of the present invention to provide a method and formulation for oral transmucosal delivery of a solid that allows for improved stability of the formulation in storage.

It is another object of at least one embodiment of the present invention to provide a method and formulation for oral transmucosal delivery of a solid that provides for increased absorption of the drug through the oral mucosal tissues.

It is another object of at least one embodiment of the present invention to provide a method and formulation for oral transmucosal delivery of a solid that allows for better control of dissolution of pharmaceutical agents.

It is another object of at least one embodiment of the present invention to provide a method and formulation for oral transmucosal delivery of a solid that does not compromise stability in storage to improve absorption.

The present invention comprises a pharmaceutical agent or drug which is capable of being absorbed into the tissues of the oral cavity or into the circulatory system through oral mucosal tissue. The pharmaceutical agent or drug is in solid form and is combined with a dissolution agent also in solid form, yielding a solid solution. The solid solution formulation may be further combined with buffers and other excipients as needed in order to facilitate the drug's manufacturing, storage, administration and delivery through oral mucosal tissue. The formulation can be used with a variety of oral transmucosal delivery dosage forms, such as a tablet, lozenge, lozenge on a stick, chewing gum, and buccal or mucosal patch.

The present invention is designed to work effectively in the unique environment of the oral cavity such that the limited amount of solvent, the relatively short period of time for drug delivery, and the pH levels within the oral cavity do not significantly deter absorption of the drug. The formulation is also designed to improve dissolution, solubility, and stability of the drug in solid solution. The advantages of the present invention contribute to the ability of the drug formulation to provide higher levels of drug absorption in oral transmucosal delivery.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are therefore not to be considered limiting of its scope, the invention will be described with additional specifics and detail through use of the accompanying drawings in which:

DETAILED DESCRIPTION OF THE PREFERRED EMBODIMENTS

Figure 1:
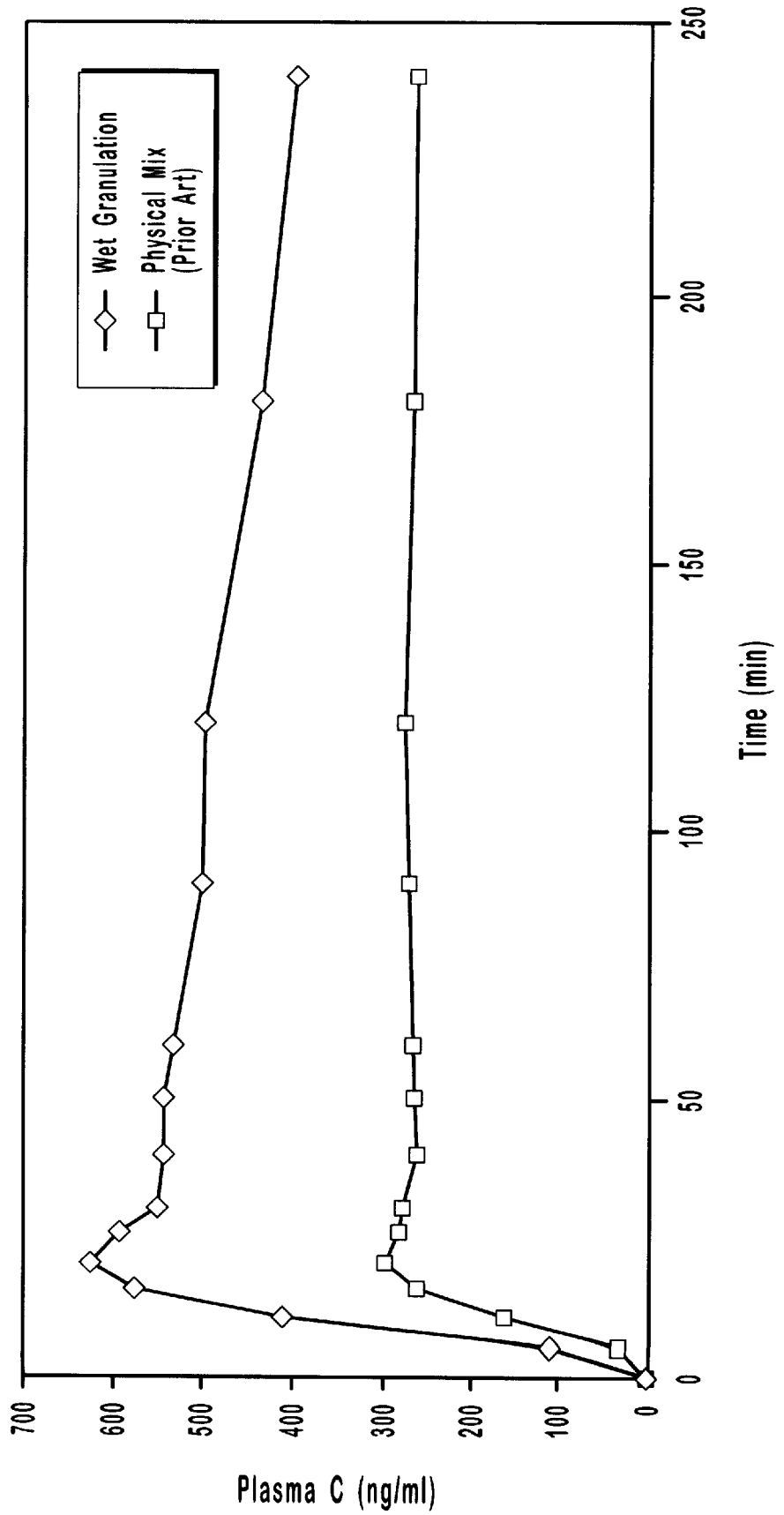
FIG. 1 is a graph showing the serum drug concentration—time profile of piroxicam as delivered by the present invention compared to delivery using the prior art.
Figure 2:
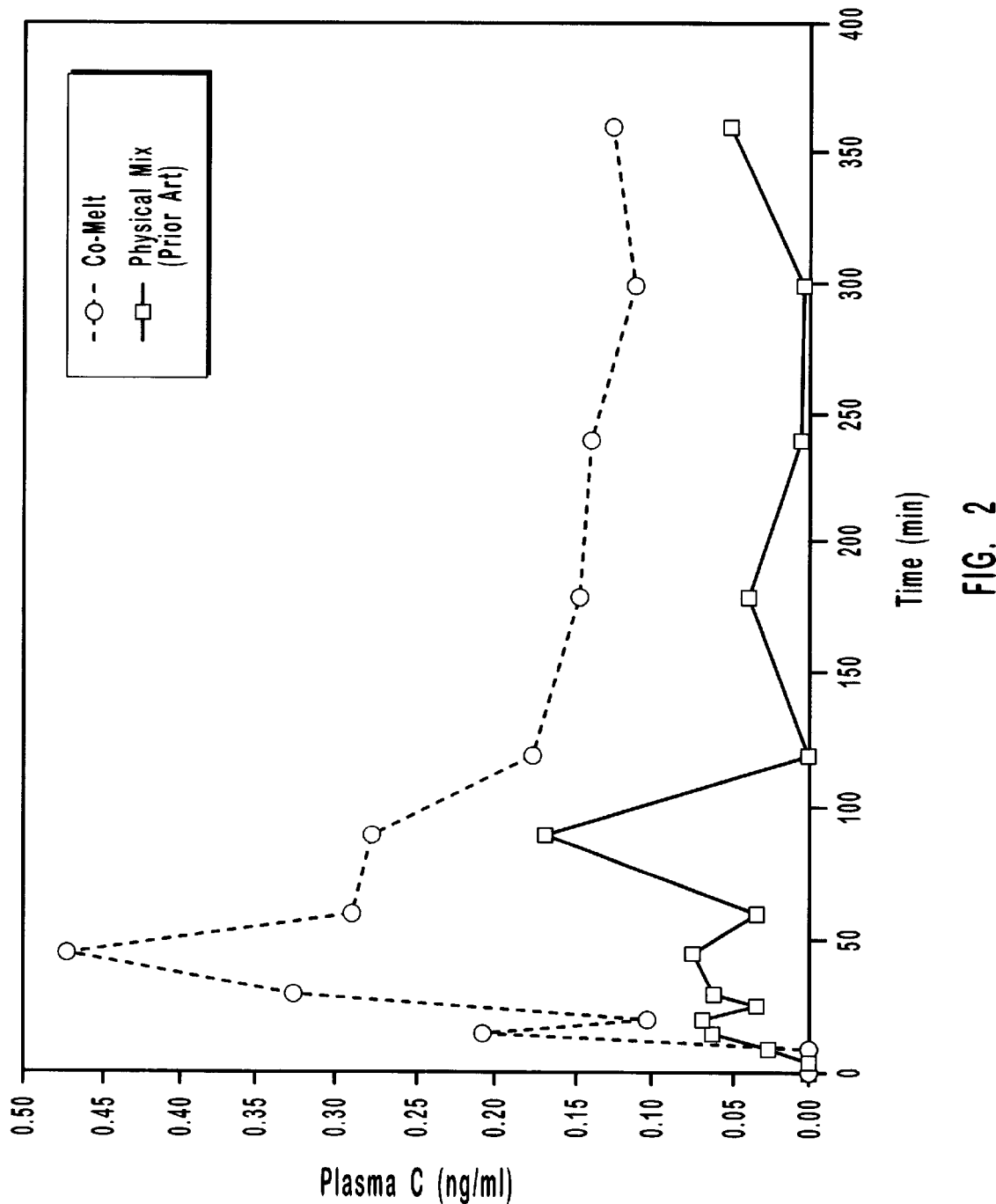
FIG. 2 is a graph showing the plasma drug concentration—time profile of droperidol 1 as delivered by the present invention compared to delivery using the prior art.
Figure 3:
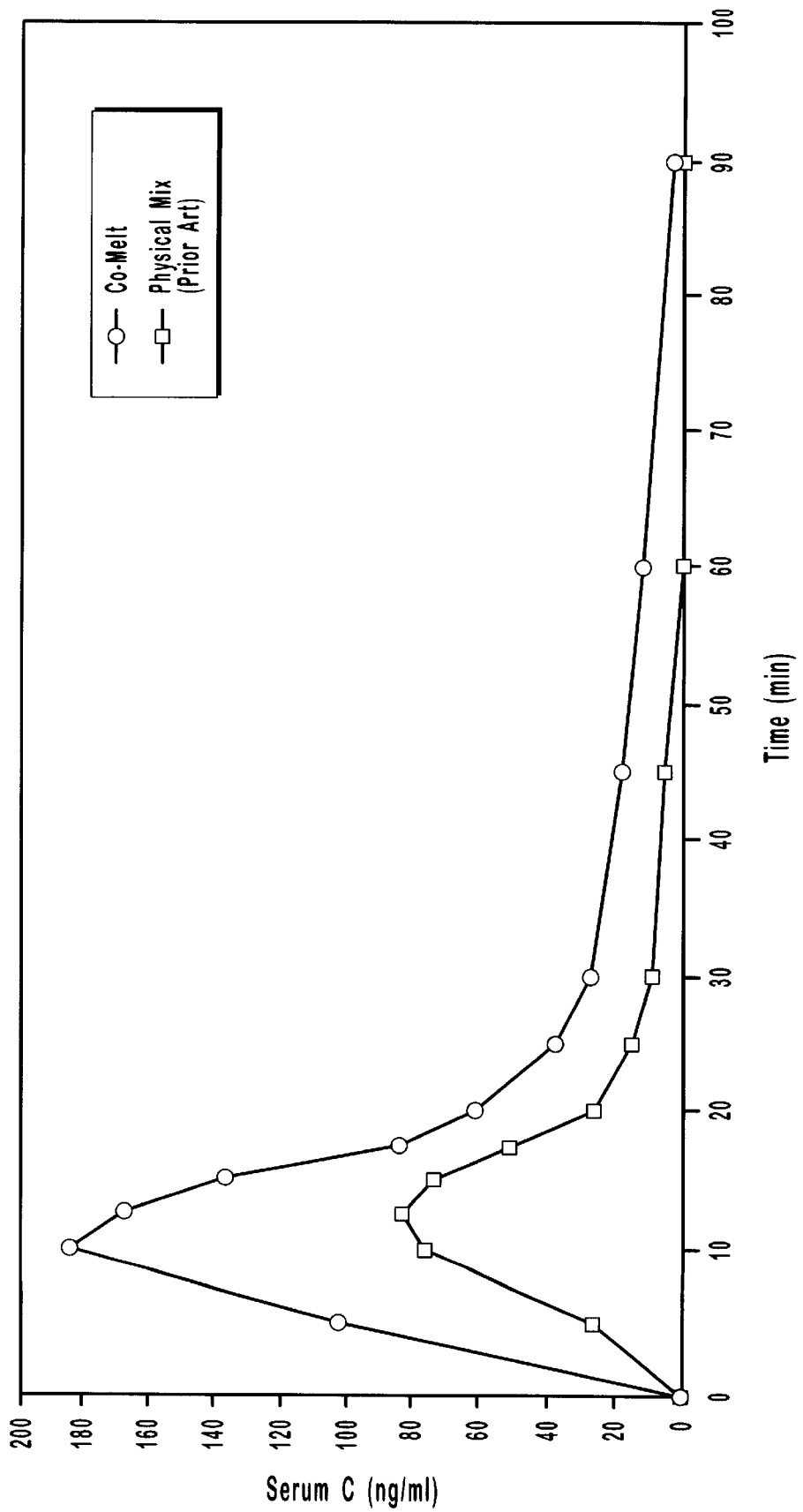
FIG. 3 is a graph showing the serum drug concentration—time profile of etomidate as delivered by the present invention compared to delivery using the prior art.

It will be readily understood that the components of the present invention, as generally described and illustrated in the Figures herein, could be arranged and designed in a wide variety of different configurations. Thus, the following more detailed description of the embodiments of the formulation and method of the present invention, as represented in FIGS. 1 through 3, is not intended to limit the scope of the invention, as claimed, but is merely representative of the presently preferred embodiments of the invention.

The present invention relates to novel methods and formulations for making solid dosage forms for oral transmucosal drug delivery. More specifically, the present invention relates to methods and formulations for making a solid solution formulation for oral transmucosal drug delivery. The present invention provides a number of advantages over the prior art formulations. The solid solution formulation comprises a pharmaceutical agent or drug capable of being delivered via the oral mucosal membrane and a dissolution agent(s) capable of being mixed with the pharmaceutical agent at the molecular level. Other pharmaceutical ingredients may be added to the formulation as necessary. The solid solution formulation provides for improved dissolution rate, solubility, and stability, and ultimately improved oral transmucosal drug delivery.

The pharmaceutical agent of the present invention may be any drug substance, which is used for diagnosis, prevention, control, and treatment of physiological, pathological and psychological conditions. It is understood that a considerable variety of drug classes and specific drugs may be used as the pharmaceutical agent or agents of the present invention. The drug classes can include without limitation: androgens, estrogens, non-steroidal anti-inflammatory agents, anti-hypertensive agents, analgesic agents, antidepressants, antibiotics, anti-cancer agents, local anesthetics, antiemetics, antiinfectants (antiinfectives), contraceptives, antidiabetic agents, steroids, antiallergy agents, antimigraine agents, agents for smoking cessation, and antiobesity agents. Specific drugs can include without limitation piroxicam, droperidol, etomidate, nicotine, testosterone, estradiol, nitroglycerin, clonidine, dexamethasone, wintergreen oil, tetracaine, lidocaine, fentanyl, sufentanil, progesterone, insulin, Vitamin A, Vitamin C, Vitamin E, prilocaine, bupivacaine, sumatriptan, dihydroergotamine, $COX_2$ inhibitors, and peptides.

The selection of dissolution agent or agents will be determined by the pharmaceutical agent, as well as the process used in making the solid solution and characteristics of its intended use. (e.g., taste for OT delivery). A primary function of the dissolution agent is to combine with the pharmaceutical agent to form a solid solution. Therefore, the dissolution agent and the pharmaceutical agent must be able to mix at the molecular level. For example, if the co-melt process is used to make a solid solution, the dissolution agent must be capable of acting as a solvent into which the pharmaceutical agent can dissolve or melt. If a partial wet granulation process is used, the dissolution agent and the pharmaceutical agent must be able to dissolve in the proper solvent for this process.

The dissolution agent may also enhance stability of the pharmaceutical agent. Since the dissolution agent is mixed with the pharmaceutical agent at the molecular level, it also provides a physical barrier for preventing the pharmaceutical agent from being contacted by other chemicals in the formulation or environment. For example, if the main degradation reaction of the pharmaceutical agent is hydrolysis, the use of a non-hygroscopic dissolution agent can block water from accessing the pharmaceutical agent. Therefore, the hydrolytic degradation reaction is prevented.

A variety of pharmaceutical ingredients can be used as the dissolution agent, depending upon the pharmaceutical agent and other ingredients used in the formulation. The dissolution agents include but are not limited to acacia, alginic acid, carbomer, carboxymethylcellulose, calcium, carboxymethylcellulose sodium, microcrystalline cellulose, cellulose, dextrates, dextrin, dextrose, ethylcellulose, fructose, gelatin, guar gum, hydroxyethyl cellulose, hydroxypropyl cellulose, hydroxypropyl methylcellulose, lactitol, lactose, lecithin, maltodextrin, mannitol, methylcellulose, poloxamer, polyethylene glycol, polymethacrylates, polyoxyethylene alkyl ethers, polyvinyl alcohol, povidone, propylene glycol alginate, sodium alginate, sodium ascorbate, sodium starch glycolate, sorbitol, starch, starch (pregelatinized), sucrose, tragacanth, trimethylglycine, xanthan gum, xylitol, and zein.

There are several ways to create a solid solution including, but not limited to, wet granulation, co-melt, spray drying, and freeze-drying.

In one embodiment of the present invention, a process of wet granulation is used to create the solid solution. The process of wet granulation can be outlined as several steps: weighing and blending of several ingredients in the presence of solvent(s), drying the mixture into solid, and milling the solid to proper size.

In the weighing and blending step of wet granulation, proper amounts of drug dissolution agent and solvent are mixed thoroughly. Additional ingredients may be added to facilitate the mixing of the ingredients. A key to this step is to find a sol-vent or solvents that both the drug and dissolution agent can dissolve into. The end result of this step is a finely blended mixture in which the drug and the dissolution agent are mixed at the molecular level.

The mixture is then dried and resized to powder so that it can be compressed into solid units. There are several ways to dry the wet granulation mixture depending on the mixture, the solvent, and the equipment. Milling and screening steps are usually used to ensure the proper particle size distribution for compression.

The wet-granulated powder may further be mixed with other ingredients to form the whole formulation. In this case, the formulation is made by a partial wet-granulation process. A formulation made using partial wet-granulation provides a unique opportunity for manufacturing ionizable compounds. As mentioned earlier, the dissolution rate, solubility, stability and permeability of an ionizable drug are greatly influenced by the pH of the system. In general, an ionized form of a drug has a higher dissolution rate and solubility, better stability, but lower permeability than does the unionized form. A partial wet granulation formulation can provide a special environment that facilitates the drug's dissolution in its local environment, yet controls the overall formulation to facilitate drug absorption. The key is the pH segregation in the solid formulation. The pH in wet granulated particles is adjusted so that the drug is ionized, i.e., low pH for a basic drug or high pH for an acidic drug. The pH in the whole formulation is adjusted so that the drug absorption is optimized. During storage, the drug is ionized and it is stable. Upon dissolution in the oral cavity, since the microenvironment of the drug favors the ionized form, the drug has a higher dissolution rate and solubility. Once the drug is in solution, the ionization of the drug is controlled by the overall environment, which is controlled by other constituents of the formulation.

In another embodiment of the present invention, a process of co-melting is used to create the solid solution. In this process, the dissolution agent is heated and melted. In its melted state, the dissolution agent can act as a solvent into which the drug is dissolved or co-melted. The mixture of drug and dissolution agent is then cooled and solidified. The solid solution of drug and dissolution agent will be further processed into compressible powder. Other ingredients may also be added to the co-melted powder to complete the drug formulation, such as ingredients which allow additional pH manipulation.

In yet another embodiment of the present invention, a process of freeze-drying is used to create the solid solution. In this process, the drug and dissolution agent are dissolved in aqueous solution. The solution is quickly frozen. The frozen solid is then put into a vacuum chamber where the water is removed from the solid via sublimation. The resulting powder is a solid solution of drug and dissolution agent.

In yet another embodiment of the present invention, a process of spray-drying is used to create the solid solution. In this process, the drug and dissolution agent are dissolved in solution. The solution is then sprayed into a chamber. The solvent is evaporated while the droplets are in the air. The result is a fine powder consisting of drug and dissolution agent.

There are many other processes for making solid solution of drug and dissolution agent, (i.e. processes that mix the drug and dissolution agent at the molecular level). The selection of the process will mainly depend on the drug and dissolution agent. The available equipment and cost will also play an important role in process selection.

The present invention provides for an increased dissolution rate of a drug using the solid solution in an oral transmucosal formulation. Because the drug is in the form of a solid solution, the dissolution rate is no longer determined by the characteristics of the drug itself, but by the dissolution profile of the solid solution. Since dissolution agents are usually selected because of their fast dissolution profiles, solid solution matrices usually dissolve quickly to release the drug in the oral cavity. The present invention provides a mechanism of controlling the drug dissolution and release by controlling the dissolution and disintegration rate of the solid unit.

The present invention may also provide for a higher solubility for certain drugs by forming a supersaturated solution upon dissolving. As mentioned earlier, the drug and dissolution agent in the form of a solid solution are mixed at the molecular level. The dissolution agents are usually selected based on their fast dissolution rate so that, upon dissolution of the dissolution agent, all the drug molecules will be in the solvent such that the drug concentration of the solution may exceed its solubility. A super saturated solution may exist until precipitation occurs. Precipitation can be viewed as three-step process: 1) the drug concentration in a solution becomes higher than its solubility; 2) drug nuclei form; and 3) the nuclei grows into crystals. More specifically, the drug concentration is a thermodynamic parameter and it determines whether crystals grow or dissolve. Nuclei form as the result of clustering of drug molecules, a kinetic process or as the result of clustering of molecules of some other solid in the solution. Crystal growth is definitely a kinetic process and therefore, the overall process of precipitation is a time-dependent, kinetic process, which does not happen instantaneously. During the time between drug dissolution and precipitation, the concentration of the drug is higher than its solubility resulting in a solution that is supersaturated. Accordingly, the present invention provides a method of creating a supersaturated solution to improve the drug absorption.

The present invention may also provide for a way to stabilize the drug in the solid formulation. Because the drug is processed and resides in micro-environment within the whole drug formulation, it is possible to create a favorable micro-environment to promote drug stability, and to promote absorption of the drug by using the rest of formulation to create a favorable environment for drug absorption. Thus the solid solution drug formulation facilitates stability without compromising drug delivery. The segregated solid formulation is therefore a unique advantage of this invention.

In order for the present invention to operate effectively, it is necessary that the drug incorporated within the dissolvable matrix be capable of permeating the mucosal membrane either alone or by suitable adjustments in the environmental pH, or other chemical modification or in combination with a suitable permeation enhancer.

The present invention has applicability to a variety of drugs affecting the central nervous system. For example, the present invention may easily be utilized in the administration of opioid agonists (such as fentanyl, alfentanil, sufentanil, lofentanil, and carfentanil), opioid antagonists (such as naloxone and nalbuphene), butyrophenones (such as droperidol and haloperidol); benzodiazepines (such as Valium, midazolam, triazolam, oxazolam, and lorazepam); GABA stimulators (such as etomidate); barbiturates (such as Thiopental, methohexital, thiamazol, pentobarbital, and hexabarbital); di-isopropylphenols drugs (such as diprivan); and other central nervous system-acting drugs such as levodopa. It will be appreciated that other drugs may also be utilized within the scope of the present invention either singly or in combination.

Table 1 lists some of the CNS-acting drugs which are suitable for incorporation into the present invention, as well as some of the characteristics of those drugs.

TABLE 1

| GENERIC DRUG | DRUG CLASS | DOSE RANGE |
| --- | --- | --- |
| methohexital | barbiturate | 10–500 mg |
| pentobarbital | barbiturate | 50–200 mg |
| thiamylal | barbiturate | 10–500 mg |
| thiopental | barbiturate | 50–500 mg |
| fentanyl | opioid agonist | 0.05–5 mg |
| alfentanil | opioid agonist | 0.5–50 mg |
| sufentanil | opioid agonist | 5–500 .mu.g |

TABLE 1-continued

| GENERIC DRUG | DRUG CLASS | DOSE RANGE |
| --- | --- | --- |
| lofentanil | opioid agonist | 0.1–100 .mu. g |
| carfentanil | opioid agonist | 0.2–100 .mu.g |
| naloxone | opioid antagonist | 0.05–5 mg |
| nalbuphene | opioid antagonist | 1–50 mg |
| diazepam | benzodiazepine | 1–40 mg |
| lorazepam | benzodiazepine | 1–4 mg |
| midazolam | benzodiazepine | 0.5–25 mg |
| oxazepam | benzodiazepine | 5–40 mg |
| triazolam | benzodiazepine | 250–1000 mg |
| droperidol | buterophenone | 1–20 mg |
| haloperidol | buterophenone | 0.5–10 mg |
| propanidid | eugenol | 1–10 mg |
| etomidate | GABA stimulator | 5–60 mg |
| propofol | substituted phenol | 3–50 mg |
| ketamine | phencyclidine | 5–300 mg |
| diprivan | substituted phenol | 5–20 mg |

Drugs having effects on the cardiovascular and renal vascular systems may also be administered using the present invention. A few examples of such drugs are identified in Table 2.

TABLE 2

| GENERIC DRUG | DRUG CLASS | DOSE RANGE |
| --- | --- | --- |
| bretylium | antiarrhythmic | 50–500 mg |
| captopril | ACE inhibitor | 25–75 mg |
| clondine | antihypertensive | 0.1–0.5 mg |
| dopamine | renal vascular | 0.5–5 mg |
| enalapril | ACE inhibitor | 5–15 mg |
| esmolol | antihypertensive/angina | 100–250 mg |
| furosemide | diuretic | 20–100 mg |
| isosorbide | angina | 2.5–40 mg |
| labetalol | antihypertensive | 100–400 mg |
| lidocaine | antiarrhythmic | 20–250 mg |
| metolazone | diuretic | 5–50 mg |
| metoprolol | antihypertensive | 25–100 mg |
| nadolol | antihypertensive | 40–160 mg |
| nifedipine | antihypertensive | 10–40 mg |
| nitroglycerin | antihypertensive/angina | 0.4–1.0 mg |
| nitroprusside | hypotensive | 10–50 mg |
| propranolol | antihypertensive/angina | 0.1–50 mg |

In addition to the foregoing, there are many other drugs which can be administered using the present invention. Exemplary of such drugs are those identified in Table 3.

TABLE 3

| GENERIC DRUG | DRUG CLASS | DOSE RANGE |
| --- | --- | --- |
| benzquinamide | antiemetic | 25–100 mg |
| meclizine | antiemetic | 25–100 mg |
| metoclopramide | antiemetic | 5–20 mg |
| prochlorperazine | antiemetic | 5–25 mg |
| trimethobenzamide | antiemetic | 100–2500 mg |
| clotrimazole | antifungal | 10–20 mg |
| nystatin | antifungal | 1,00,000–500,000 units |
| cardidopa | antiparkinson with levodopa | 10–50 mg |
| levodopa | antiparkinson | 100–750 mg |
| sucralfate | antisecretory | 1–2 grams |
| albuterol | bronchodilator | 0.8–1.6 mg |
| aminophylline | bronchodilator | 100–500 mg |
| beclomethasone | bronchodilator | 20–50 mu.g |
| dyphylline | bronchodilator | 100–400 mg |
| epinephrine | bronchodilator | 200–500 .mu.g |
| flunisolide | bronchodilator | 25–50 .mu.g |
| isoetharine | bronchodilator | 170–680 .mu.g |
| isoproterenol HCl | bronchodilator | 60–260 .mu.g |
| metaproterenol | bronchodilator | 0.65–10 mg |

TABLE 3-continued

| GENERIC DRUG | DRUG CLASS | DOSE RANGE |
|---|---|---|
| oxtriphylline | bronchodilator | 50–400 mg |
| terbutaline | bronchodilator | 2.5–10 mg |
| theophylline | bronchodilator | 50–400 mg |
| ergotamine | antimigraine | 2–4 mg |
| methysergide | antimigraine | 2–4 mg |
| propranolol | antimigraine | 80–160 mg |
| suloctidil | antimigraine | 200–300 mg |
| ergonovine | oxytocic | 0.2–0.6 MG |
| oxytocin | oxytocic | 5–20 units |
| desmopressin acetate | antidiuretic | 10–50 .mu.g |
| lypressin | antidiuretic | 7–14 .mu.g |
| vasopressin | antidiuretic | 2.5–60 units |
| insulin | antihyperglycemic | 1–100 units |

In addition to the foregoing drugs, certain macromolecular drugs (such as beta.-endorphin, enkephalins, bradykinin, aniotensin I, gonadotropic hormones, adrenocorticotropic hormone (ACTH), calcitonin, parathyroid hormone, and growth hormone), polysaccharides (such as heparin), antigens, antibodies, and enzymes may be adapted for transmucosal administration within the scope of the present invention.

Pharmaceutical ingredients that can be used in the formulation of the present invention may include, but are not limited to, absorbents, buffering agents (such as phosphate buffer, carbonate buffer, tris buffer, tartrate buffer, borate buffer, acetate buffer, or maleate buffer), colorants, flavorants, solvents and co-solvents, coating agents, direct compression excipients, disintegrants, glidants, lubricants, opaquants, polishing agents, suspending agents, sweetening agents, anti-adherents, binders, and capsule diluents, the ingredients may also include anti-fungal preservatives, anti-microbial preservatives, clarifying agents, emulsifying agents, antioxidants, levigating agents, plasticizers, surfactants, tonicity agents, and viscosity increasing agents.

EXAMPLE 1

In one actual experiment, oral transmucosal delivery of a pharmaceutical agent using the present invention was compared with oral transmucosal delivery of the same pharmaceutical agent using a prior art technique of physically mixing the drug formulation. The drug formulation included the ingredients piroxicam, mannitol, Emdex® (dextrates, hydrated), sodium hydroxide, and magnesium stearate in the weight percentages and amounts per unit shown in Table A.

TABLE A

Piroxicam Oral Transmucosal Delivery Formulation

| Ingredient | % | mg/2g |
|---|---|---|
| Piroxicam | 2% | 40 |
| Mannitol | 10% | 200 |
| Emdex ® (dextrates, hydrated) | 86.76% | 1735.2 |
| NaOH | 0.24% | 4.8 |
| Mg Stearate | 1% | 20 |
| Total | 100% | 2000 |

The physical mix formulation was prepared using a prior art method by (1) mixing all the ingredients except for magnesium stearate in a container, (2) mixing in magnesium stearate with the other ingredients, (3) compressing said ingredients with a Carver press at 3,000 psi.

To prepare the formulation of the present invention, a process of wet granulation was used. The steps in this example included (1) mixing piroxicam, mannitol, sodium hydroxide and water, (2) drying the mixture in an oven at 40° centigrade for 48 hours to form a dried paste, (3) grinding the dried paste, (4) mixing the paste with the remaining ingredients except for magnesium stearate, (5) adding magnesium stearate and mixing again, and (6) compressing said ingredients with a carver press at 3,000 PSI. The physically mixed formulation (PM) and wet granulation formulation (WG) below, were administered oral transmucosally as part of an in vivo dog study. The results of the study are shown in Tables B-1 and B-2 below as well as in FIG. 1.

TABLE B-1

Piroxicam Serum Concentration (ng/ml)
After OT Delivery of Physical Mix Formulation in Dog Studies

| Time | PM#1 | PM#2 | Average | SD |
|---|---|---|---|---|
| 0.00 | 0.00 | 0.00 | 0.00 | 0.00 |
| 5 | 40.01 | 25.74 | 32.88 | 10.09 |
| 10 | 176.68 | 149.78 | 163.23 | 19.02 |
| 15 | 289.08 | 231.90 | 260.49 | 40.43 |
| 20 | 316.51 | 278.19 | 297.35 | 27.10 |
| 25 | 307.93 | 257.80 | 282.87 | 35.45 |
| 30 | 294.62 | 256.79 | 275.71 | 26.75 |
| 40 | 275.78 | 249.79 | 262.79 | 18.38 |
| 50 | 269.81 | 264.78 | 267.30 | 3.56 |
| 60 | 269.20 | 265.01 | 267.11 | 2.96 |
| 90 | 260.02 | 283.04 | 271.53. | 16.28 |
| 120 | 257.05 | 298.86 | 277.96 | 29.56 |
| 180 | 242.79 | 298.41 | 270.60 | 39.33 |
| 240 | 235.76 | 301.22 | 268.49 | 46.29 |
| Cmax | 316.51 | 278.19 | 297.35 | 27.10 |
| tmax | 20 | 20 | 20.00 | 0.00 |
| AUC | 59708.65 | 65969.975 | 62839.31 | 4427.43 |

TABLE B-2

Serum Piroxican Concentration (ng/ml)
After OT Delivery of Wet Granulation Formulation in Dog Studies

| Time | WG#1 | WG#2 | Average | SD |
|---|---|---|---|---|
| 0.00 | 0.00 | 0.00 | 0.00 | 0.00 |
| 5 | 120.20 | 102.05 | 111.13 | 12.83 |
| 10 | 463.26 | 358.84 | 411.05 | 73.84 |
| 15 | 654.54 | 502.39 | 578.47 | 107.59 |
| 20 | 754.35 | 497.11 | 625.73 | 181.90 |
| 25 | 702.33 | 485.14 | 593.74 | 153.58 |
| 30 | 643.74 | 456.46 | 550.10 | 132.43 |
| 40 | 613.86 | 474.65 | 544.26 | 98.44 |
| 50 | 631.56 | 459.09 | 545.33 | 121.95 |
| 60 | 625.78 | 443.70 | 534.74 | 128.75 |
| 90 | 591.54 | 416.34 | 503.94 | 123.89 |
| 120 | 578.42 | 426.69 | 502.56 | 107.29 |
| 180 | 543.28 | 338.04 | 440.66 | 145.13 |
| 240 | 484.20 | 329.63 | 406.92 | 109.30 |
| Cmax | 754.35 | 502.39 | 628.37 | 178.16 |
| tmax | 20 | 15 | 17.50 | 3.54 |
| AUC | 134169.15 | 93225.05 | 113697.10 | 28951.85 |

The data show an increase in both the maximum blood concentration, ($C_{max}$), and bioavailability (AUC). The increase of the $C_{max}$ is more than two fold and the increase in AUC is almost two-fold. The data also show faster absorption into the blood stream ($t_{max}$).

EXAMPLE 2

In another experiment, the plasma concentrations of the drug droperidol delivered oral transmucosally using the present invention employing a co-melt technique were compared to those of droperidol delivered oral transmucosally using a prior art technique of physically mixing the drug formulation. The ingredients included droperidol, polyethylene glycol, citric acid in sorbitol, and solvent. The ingredients were mixed in the amounts shown in Table C.

TABLE C

| Ingredient | % | mg/2g |
|---|---|---|
| Droperidol | 0.05% | 1 |
| Sorbitol | 82.95% | 1659 |
| polyethyleneglycol (PEG) | 15% | 300 |
| pH 6.0 Na2PH04/ citric acid (2:15:1) in sorbitol | 2% | 40 |

The prior art formulation was prepared by physically mixing the ingredients and compressing them into solid units. The present invention formulation was prepared by heating droperidol and PEG in a 90° C. water bath until the PEG was melted. The mixture was then cooled, solidified, and milled into powder. The co-melt powder was mixed with the other ingredients and compressed into solid units. The pharmaceutical agents were delivered oral transmucosally as part of an in vivo dog study. The blood plasma drug concentrations (Table D) of the subjects were measured over a period of 6 hours.

TABLE D

Plasma Droperidol Concentrations After OT Delivery to Dogs
Droperidol Physical Mix vs. Co-Melt

| Time (min) | Co-melt | PM |
|---|---|---|
| 0 | 0.00 | 0.00 |
| 5 | 0.00 | 0.00 |
| 10 | 0.00 | 0.03 |
| 15 | 0.21 | 0.06 |
| 20 | 0.10 | 0.07 |
| 25 |  | 0.03 |
| 30 | 0.33 | 0.06 |
| 45 | 0.47 | 0.08 |
| 60 | 0.29 | 0.04 |
| 90 | 0.28 | 0.17 |
| 120 | 0.18 | 0.00 |
| 180 | 0.15 | 0.04 |
| 240 | 0.14 | 0.01 |
| 300 | 0.12 | 0.01 |
| 360 | 0.13 | 0.05 |
| Cmax | 0.47 | 0.17 |
| tmax | 45 | 90 |
| AUC(ng/ml*min) | 62.89 | 13.26 |

As shown in Table D and in FIG. 2, the data strongly suggest that the drug is absorbed from the present invention at a higher rate and to a greater extent compared to the physical mix formulation. the present invention formulation is more readily absorbed and absorbed in higher quantities into the systemic circulation than the prior art formulation.

EXAMPLE 3

In yet another experiment employing the co-melt process, the oral transmucosal delivery of the drug etomidate using the present invention was compared with delivery using prior art methods. The drug formulations were prepared using the ingredients Etomidate, PEG and Sorbitol. The amounts of each ingredient in the formulations are shown in Table E.

TABLE E

| Ingredient | % | mg/2g |
|---|---|---|
| Etomidate | 1.25 | 25 |
| PEG | 74.06 | 1481.25 |
| Sorbitol | 24.69 | 493.75 |

The prior art formulation was prepared using a process of physical mixing. The present invention formulation was prepared using a co-melting process to create a solid solution containing etomidate. The two formulations were administered oral transmucosally as part of an in vivo dog study. Serum concentrations of the drug were measured over a 90 minute period. The results are shown in Tables F-1 and F-2 and in FIG. 3.

TABLE F-1

Serum Concentration (ng/ml) of Etomidate after OT Delivery of Co-melt Formulation

| Time (min) | #4-200 | #4-210 | #4-222 | Average | S.D. | R.S.D |
|---|---|---|---|---|---|---|
| 0.0 | 0.00 | 0.00 | 0.00 | 0.00 | 0.00 |  |
| 5.0 | 103.98 | 93.00 | 111.89 | 102.95 | 9.48 | 9.21% |
| 10.0 | 172.32 | 165.00 | 213.92 | 183.75 | 26.39 | 14.36% |
| 12.5 | 138.13 | 156.00 | 210.04 | 168.06 | 37.44 | 22.28% |
| 15.0 | 121.50 | 121.00 | 168.59 | 137.03 | 27.33 | 19.94% |
| 17.5 | 77.06 | 71.00 | 104.53 | 84.20 | 17.87 | 21.22% |
| 20.0 | 64.82 | 53.00 | 69.50 | 62.44 | 8.50 | 13.62% |
| 25.0 | 41.70 | 31.00 | 43.22 | 38.64 | 6.66 | 17.24% |
| 30.0 | 33.81 | 20.00 | 28.96 | 27.59 | 7.00 | 25.39% |
| 45.0 | 21.33 | 15.00 | 17.63 | 17.99 | 3.18 | 17.67% |
| 60.0 | 13.42 | 10.00 | 13.66 | 12.36 | 2.05 | 16.57% |
| 90.0 | 9.97 | 0.00 | 0.00 | 3.32 | 5.75 | 173.21% |
| Cmax | 172.32 | 165.00 | 213.92 | 183.75 |  |  |
| Tmax | 10 | 10 | 10 | 10.00 |  |  |
| AUC | 3568.76 | 2957.5 | 3907.74 | 3478.00 |  |  |

TABLE F-2

Serum Concentration (ng/ml) of Etornidate after OT Delivery of Physical Mix Formulation

| Time(min) | #4-200 | #4-210 | #4-222 | Average | S.D. | R.S.D |
|---|---|---|---|---|---|---|
| 0.0 | 0.00 | 0.00 | 0.00 | 0.00 | 0.00 |  |
| 5.0 | 34.43 | 29.11 | 16.17 | 26.57 | 9.39 | 35.35% |
| 10.0 | 103.12 | 81.86 | 46.59 | 77.19 | 28.55 | 36.99% |
| 12.5 | 113.48 | 81.71 | 54.99 | 83.40 | 29.28 | 35.11% |
| 15.0 | 87.68 | 85.63 | 50.67 | 74.66 | 20.80 | 27.86% |
| 17.5 | 49.64 | 72.13 | 33.80 | 51.85 | 19.26 | 37.14% |
| 20.0 | 32.97 | 28.41 | 16.91 | 26.10 | 8.28 | 31.71% |
| 25.0 | 19.31 | 16.02 | 10.58 | 15.30 | 4.41 | 28.80% |
| 30.0 |  | 19.02 | 0.00 | 9.51 | 13.45 | 141.42% |
| 45.0 | 11.17 | 5.54 | 0.00 | 5.57 | 5.58 | 100.25% |
| 60.0 |  | 0.00 | 0.00 | 0.00 | 0.00 |  |
| 90.0 | 0.00 | 0.00 | 0.00 | 0.00 | 0.00 |  |
| Cmax | 113.48 | 85.63 | 54.99 | 84.70 |  |  |
| Tmax | 12.5 | 15 | 12.5 | 13.33 |  |  |
| AUC | 1913.79 | 1511.14 | 720.523 | 1381.82 |  |  |

As with the other experiments, the data show that etomidate is absorbed at a faster rate and to a greater extent (increased bioavailability) when delivered using the present invention.

What is claimed is:

1. An improved oral transmucosal solid dosage form drug delivery formulation comprising:

a pharmaceutical agent capable of being absorbed into oral mucosal tissue having a dissolution rate in the solvents found in the oral cavity, a dissolution agent having a dissolution rate in the solvents found in the oral cavity, said dissolution rate of said dissolution agent being greater than said dissolution rate of said pharmaceutical agent, and said pharmaceutical agent being in solid solution with said dissolution agent.

2. The formulation of claim 1 further comprising a buffer system.

3. The formulation of claim 2 wherein said buffer system is capable of maintaining a significant portion of said pharmaceutical agent in unionized form following dissolution of said pharmaceutical agent.

4. The formulation system of claim 2, wherein a for said system is chosen from the group consisting of: phosphate, carbonate, tris, tartrate, borate, acetate, or maleate buffer.

5. The delivery system of claim 1, wherein said dissolution agent provides a physical barrier between pharmaceutical agent and said buffer while in storage.

6. The formulation of claim 4, wherein said pharmaceutical agent is unionizable.

7. The formulation of claim 6, wherein said pharmaceutical agent is an organic acid.

8. The formulation of claim 6, wherein said pharmaceutical agent is an organic base.

9. The formulation of claim 1, wherein said pharmaceutical agent is selected from the group consisting of: androgen, estrogen, non-steroidal anti-inflammatory agents, anti-hypertensive agents, analgesic agents, antidepressants, antibiotics, anti-cancer agents, local anesthetics, antiemetics, antiinfectives, contraceptives, antidiabetic agents, steroids, antiallergy agents, antimigraine agents, agents for smoking cessation, and antiobesity agents.

10. The formulation of claim 1, wherein said pharmaceutical agent has an ionized form that is more stable in storage and more soluble in a solvent than the agent's unionized form.

11. The formulation of claim 1, wherein said pharmaceutical agent has an unionized form that is more permeable than the agent's ionized form.

12. The formulation of claim 1, wherein said pharmaceutical agent is brought into solution with said dissolution agent through the process of co-melting to form a solid solution.

13. The formulation of claim 1, wherein said pharmaceutical agent is brought into solution with said dissolution agent through the process of dissolving and freeze-drying to form a solid solution.

14. The formulation of claim 1, wherein said pharmaceutical agent is brought into solution with said dissolution agent through the process of wet granulation to form a solid solution.

15. The formulation of claim 1, wherein said pharmaceutical agent is brought into solution with said dissolution agent through the process of partial wet granulation to form a solid solution.

16. The formulation of claim 1, wherein said pharmaceutical agent is brought into solution with said dissolution agent through the process of dissolving and spray drying to form a solid solution.

17. The formulation of claim 1, wherein said pharmaceutical agent in solution with said dissolution agent provides a faster dissolution rate for said pharmaceutical agent.

18. The formulation of claim 1, wherein said pharmaceutical agent in solution with said dissolution agent provides more free drug for absorption.

19. The formulation of claim 1, wherein said pharmaceutical agent combined in solution with said dissolution agent provides an increased solubility for said pharmaceutical agent.

20. The formulation of claim 1, wherein said dissolution agent is selected from the group consisting of: acacia, alginic acid, carbomer, carboxymethylcellulose, calcium, carboxymethylcellulose sodium, microcrystalline cellulose, cellulose, dextrates, dextrin, dextrose, ethylcellulose, fructose, gelatin, guar gum, hydroxyethyl cellulose, hydroxypropyl cellulose, hydroxypropyl methylcellulose, lactitol, lactose, lecithin, maltodextrin, mannitol, methylcellulose, poloxamer, polyethylene glycol, polymethacrylates, polyoxyethylene alkyl ethers, polyvinyl alcohol, propylene glycol alginate, sodium alginate, sodium ascorbate, sodium starch glycolate, sorbitol, starch, starch (pregelatinized), sucrose, tragacanth, trimethylglycine, xanthan gum, xylitol, or zein.

21. The delivery system of claim 1, wherein said dissolution agent controls the rate of dissolution of said pharmaceutical agent.

22. The formulation of claim 1, wherein said formulation is disposed within a oral transmucosal patch.

23. The formulation of claim 1, wherein said formulation is in a lozenge/troche dosage form.

24. The formulation of claim 1, wherein said formulation is in a lollipop dosage form.

25. The formulation of claim 1, wherein said formulation is in a chewing gum dosage form.

26. The delivery system of claim 1, further comprising at least one pharmaceutical ingredient selected from the group consisting of: absorbents, buffering agents, colorants, flavorants, solvents and co-solvents, coating agents, direct compression excipients, disintegrants, glidants, lubricants, opaquants, polishing agents, suspending agents, sweetening agents, anti-adherents, binders, and capsule diluents, antifungal preservatives, antimicrobial preservatives, clarifying agents, emulsifying agents, antioxidants, levigating agents, plasticizers, surfactants, tonicity agents, and viscosity increasing agents.

27. The formulation of claim 1, wherein said pharmaceutical agent is selected from the group of: piroxicam, droperidol, etomidate, nicotine, testosterone, estradiol, nitroglycerin, clonidine, dexamethasone, wintergreen oil, tetracaine, lidocaine, fentanyl, sufentanil, progestrone, insulin, Vitamin A, Vitamin C, Vitamin E, prilocaine, bupivacaine, sumatriptan, dihydroergotamine, $COX_2$ inhibitors, and peptides.

28. The formulation of claim 1, wherein said pharmaceutical agent is chosen from the group consisting of: methohexital, pentobarbital, thiamylal, thiopental, fentanyl, alfentanil, sufentanil, lofentanil, carfentanil, naloxone, epam, lorazepam, midazolam, oxazepam, triazolam, droperidol, propanidid, etomidate, propofol, ketamine, diprivan, bretylium, captopril, clonidine, dopamine, enalapril, esmolol, furosemide, isosorbide, labetalol, lidocaine, metolazone, metoprolol, nadolol, nifedipine, nitroglycerin, nitroprusside, propranolol, benzquinamide, meclizine, metoclopramide, prochlorperazine, trimethobenzamide, clotrimazole, nystatin, carbidopa, levodopa, sucralfate, albuterol, amninophylline, beclomethasone, dyphylline, epinephrine, flunisolide, isoetharine, isoproterenol HCl, metaproterenol, oxtriphylline, terbutaline, theophylline, ergotamine, methysergide, propranolol, suloctidil, ergonovine, oxytocin, desmopressin, acetate, lypressin, vasopressin, insulin, beta-endorphin, enkephalins, bradykinin, aniotensin I, gonadotropic hormones, adrenocorticotropic hormone (ACTH), calcitonin, parathyroid hormone, growth hormone, polysaccharides (such as heparin), antigens, antibodies, and enzymes.

29. The formulation of claim 1, wherein said pharmaceutical agent belongs to a drug class chosen from the group consisting of: barbiturate, opioid agonist, benzodiazepine, buterophenone, eugenol, GABA stimulator, substituted phenol, phencyclidine, antiarrhythmic, ACE inhibitor, antihypertensive, renal vascular, antihypertensive/angina, diuretic, angina, hypotensive, antiemetic, antifungal, antiparkinson with levodopa, antiparkinson, antisecretory, bronchodilator, antimigraine, oxytocic, antidiuretic, and antihyperglycemic.

30. A method for oral transmucosal delivery of a pharmaceutical agent comprising the steps of:
providing a drug formulation comprising a solid pharmaceutical agent in solid solution with a dissolution agent,
administering said drug formulation into a patient's oral cavity, and
delivering said pharmaceutical agent by absorption through a patient's oral mucosal tissue.

31. The method of claim 30, wherein the step of providing a drug formulation further comprises a buffer system.

32. The method of claim 30, wherein said buffer maintains a pH level such that ionization of said pharmaceutical is controlled by said buffer system.

33. The method of claim 30, wherein said drug formulation further comprises at least one excipient.

34. The method of claim 30, wherein said pharmaceutical agent is an unionizable compound.

35. The method of claim 34, wherein said pharmaceutical agent is an organic base.

36. The method of claim 34, wherein said pharmaceutical agent is an organic acid.

37. The method of claim 33, wherein said pharmaceutical agent is selected from the group of: androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, and anti-obesity agents. Specific drugs can include without limitation piroxicam, droperidol, etomidate, nicotine, testosterone, estradoil, nitroglycerin, clonidine, dexamethasone, wintergreen oil, tetracaine, lidocaine, fentanyl, sufentanil, progestrone, insulin, Vitamin A, Vitamin C, Vitamin E, prilocaine, .

38. The method of claim 30, wherein said dissolution agent is selected from the group of acacia, alginic acid, carbomer, carboxymethylcellulose, calcium, carboxymethylcellulose sodium, microcrystalline cellulose, cellulose, dextrates, dextrin, dextrose, ethylcellulose, fructose, gelatin, guar gum, hydroxyethyl cellulose, hydroxypropyl cellulose, hydroxypropyl methylcellulose, latitol, lactose, lecithin, maltodextrin, mannitol, methylcellulose, poloxamer, polyethylene glycol, polymethacrylates, polyoxyethylene alkyl, ethers, polyvinyl alcohol, povidone, propylene glycol alginate, sodium alginate, sodium ascorbate, sodium starch glycolate, sorbitol, starch, starch (pregelatinized), sucrose, tragacanth, trimethylglycine, xanthan gum, xylitol, or zein.

39. The method of claim 30, wherein said pharmaceutical agent and said dissolution agent are combined in solution through a process of co-melting.

40. The method of claim 30, wherein said pharmaceutical agent and said dissolution agent are combined in solution through a process of dissolving and freeze-drying.

41. The method of claim 30, wherein said pharmaceutical agent and said dissolution agent are combined in solution through a process of wet granulation.

42. The method of claim 30, wherein said pharmaceutical agent and said dissolution agent are combined in solution through a process of partial wet granulation.

43. The method of claim 27, wherein said pharmaceutical agent and said dissolution agent are combined in solution through a process of dissolving and spray drying.

44. The method of claim 30, wherein said step of administering said drug formulation into a patient's oral cavity comprises disposing said drug formulation within the oral cavity, said drug formulation having a lozenge trache dosage form.

45. The method of claim 30, wherein the step of administering said drug formulation comprises disposing said drug formulation within the oral cavity of the patient, said drug formulation having a lollipop dosage form.

46. The method of claim 30, wherein the step of delivering said pharmaceutical agent comprises maintaining said drug formulation in the patient's oral cavity for a period of time sufficient to dissolve said drug formulation.

47. The method of claim 30, wherein said oral mucosal tissue is located in a patient's pharynx.

48. The method of claim 30, wherein said oral mucosal tissue is in a patient's esophagus.

49. The method of claim 30, wherein said pharmaceutical agent is chosen from the group consisting of: methohexital, pentobarbital, thiamylal, thiopental, fentanyl, alfentanil, sufentanil, lofentanil, carfentanil, naloxone, epam, lorazepam, midazolam, oxazepam, triazolam, droperidol, propanidid, etomidate, propofol, ketamine, diprivan, bretylium, captopril, clonidine, dopamine, enalapril, esmolol, furosemide, isosorbide, labetalol, lidocaine, metolazone, metoprolol, nadolol, nifedipine, nitroglycerin, nitroprusside, propranolol, benzquinamide, meclizine, metoclopramide, prochlorperazine, trimethobenzamide, clotrimazole, nystatin, carbidopa, levodopa, sucralfate, albuterol, aminophylline, beclomethasone, dyphylline, epinephrine, flunisolide, isoetharine, isoproterenol Hcl, metaproterenol, oxtriphylline, terbutaline, theophylline, ergotamine, methysergide, propranolol, suloctidil, ergonovine, oxytocin, desmopressin, acetate, lypressin, vasopressin, insulin, beta-endorphin, enkephalins, bradykinin, aniotensin I, gonadotropic hormones, adrenocorticotropic hormone (ACTH), calcitonin, parathyroid hormone, and growth hormone), polysaccharides (such as heparin), antigens, antibodies, or enzymes.

50. The method of claim 30, wherein said pharmaceutical agent belongs to a class of drugs chosen from the group consisting of: barbiturate, opioid agonist, opioid antagonist, benzodiazepine, buterophenone, eugenol, GABA stimulator, substituted phenol, phencyclidine, or substituted phenol.

51. An oral mucosal drug formulation comprising:
a solid solution micro-environment within the drug formulation,
a drug and a dissolution agent disposed within the solid solution micro-environment, and
a pharmaceutical ingredient segregated from the micro-environment.

52. The formulation of claim 51, wherein said micro-environment facilitates rapid dissolution of the drug in solvents of in the oral mucosal cavity.

53. The formulation of claim 51, wherein said micro-environment acts as a physical barrier between said drug and said pharmaceutical ingredient.

54. The formulation of claim 51, wherein said pharmaceutical ingredient improves absorption of the drug.

55. The formulation of claim 51, wherein said micro-environment permits dissolution of the drug in a free state.

* * * * *